United States Patent
Giannulli et al.

(10) Patent No.: US 11,636,350 B1
(45) Date of Patent: Apr. 25, 2023

(54) SYSTEMS AND METHODS FOR AUTOMATED SCRIBES BASED ON KNOWLEDGE GRAPHS OF CLINICAL INFORMATION

(71) Applicant: AMERICAN MEDICAL ASSOCIATION, Chicago, IL (US)

(72) Inventors: Thomas Giannulli, Newport Beach, CA (US); Joshua Samuel Schwartz, Laguna Niguel, CA (US)

(73) Assignee: American Medical Association, Chicago, IL (US)

( * ) Notice: Subject to any disclaimer, the term of this patent is extended or adjusted under 35 U.S.C. 154(b) by 364 days.

(21) Appl. No.: 16/906,910

(22) Filed: Jun. 19, 2020

Related U.S. Application Data

(60) Provisional application No. 62/964,020, filed on Jan. 21, 2020, provisional application No. 62/864,764, filed on Jun. 21, 2019.

(51) Int. Cl.
| | |
|---|---|
| *G06F 17/00* | (2019.01) |
| *G06N 5/02* | (2023.01) |
| *G06K 9/62* | (2022.01) |
| *G16H 50/70* | (2018.01) |
| *G16H 10/60* | (2018.01) |
| *G06V 30/40* | (2022.01) |

(52) U.S. Cl.
CPC .............. *G06N 5/02* (2013.01); *G06K 9/6296* (2013.01); *G06V 30/40* (2022.01); *G16H 10/60* (2018.01); *G16H 50/70* (2018.01)

(58) Field of Classification Search
CPC .......... G06N 5/02; G16H 10/60; G16H 50/70; G06V 30/40; G06K 9/6296
See application file for complete search history.

(56) References Cited

U.S. PATENT DOCUMENTS

| | | | |
|---|---|---|---|
| 10,025,852 B2 * | 7/2018 | Breedvelt-Schouten | ..................... G06F 16/338 |
| 10,365,792 B2 * | 7/2019 | Emanuel | ............... G06F 3/0482 |
| 10,963,476 B2 * | 3/2021 | Cady | ..................... G06F 16/248 |

(Continued)

OTHER PUBLICATIONS

"Semantic Health Knowledge Graph: Semantic Integration of Heterogeneous Medical Knowledge and Services"; Longxiang Shi et, al; Feb. 12, 2017; 13 pages.*

*Primary Examiner* — Mohammed H Zuberi
(74) *Attorney, Agent, or Firm* — Faegre Drinker Biddle & Reath

(57) ABSTRACT

According to certain embodiments, the present disclosure includes a method for generating a knowledge graph of clinical information for use as a reference model to semantically represent relevant information from clinical encounters. In certain embodiments, the method includes representing a clinical concern as a module of the knowledge graph. In some examples, the method includes associating at least one section node with the module, wherein each section node of the at least one section node corresponds to a clinical concept relevant to the clinical concern and associating at least one topic node with the at least one section node, wherein each topic node of the at least one topic node corresponds to a clinical topic relevant to the clinical concept. And, in certain embodiments the method includes outputting the knowledge graph of clinical information to semantically represent the relevant information from a clinical encounter associated with the clinical concern.

14 Claims, 9 Drawing Sheets

(56) References Cited

U.S. PATENT DOCUMENTS

| | | | |
|---|---|---|---|
| 2013/0212093 A1* | 8/2013 | Chitiveli | G06F 16/338 |
| | | | 707/730 |
| 2018/0108443 A1* | 4/2018 | Li | G16H 20/10 |
| 2018/0322954 A1* | 11/2018 | Ding | G16H 70/60 |
| 2021/0182606 A1* | 6/2021 | Maroo | G06K 9/6256 |

* cited by examiner

SYSTEMS AND METHODS FOR AUTOMATED SCRIBES BASED ON KNOWLEDGE GRAPHS OF CLINICAL INFORMATION

CROSS-REFERENCE TO RELATED APPLICATIONS

This application claims priority to Provisional Application No. 62/864,764, filed Jun. 21, 2019 and Provisional Application No. 62/964,020, filed Jan. 21, 2020, both of which are incorporated herein by reference in their entireties for all purposes.

FIELD OF THE DISCLOSURE

The present disclosure relates to healthcare technology; and, more specifically, the present disclosure relates to generating and/or applying a knowledge graph of clinical information, in accordance with certain embodiments.

BACKGROUND OF THE DISCLOSURE

According to certain embodiments, the evolution of digital medicine has increased the demand for structured and concise clinical information to better access clinical quality, disease outcomes, and provider performance. As such, in some examples, the demands for more granular, codified and/or structured data has resulted in the increase in provider data entry burden through the use of complex software and/or data entry systems. In certain embodiments, the human hardware and/or software interface is a barrier to personalized care in many cases, and it has reduced the joy of practicing medicine and increased the frustration of providers. Embodiments disclosed herein alleviate some of these issues.

SUMMARY OF THE DISCLOSURE

The present disclosure relates to generating and/or applying a knowledge graph of clinical information. Embodiments include but are not limited to the following examples.

In an Example 1, a computer-implemented method for generating a knowledge graph of clinical information for use as a reference model to semantically represent relevant information from clinical encounters, comprises: representing a clinical concern as a module of the knowledge graph of clinical information; associating at least one section node with the module, wherein each section node of the at least one section node corresponds to a clinical concept relevant to the clinical concern; associating at least one topic node with the at least one section node, wherein each topic node of the at least one topic node corresponds to a clinical topic relevant to the clinical concept; and outputting the knowledge graph of clinical information to semantically represent the relevant information from a clinical encounter associated with the clinical concern.

In an Example 2, the method of Example 1, wherein the at least one section node corresponds to at least one of the following clinical concepts: history of present illness, review of systems, examination, history, diagnosis, and care plan.

In an Example 3, the method of Example 1, wherein the at least one topic node corresponds to at least one of the following clinical topics: onset, location, pain, alleviating factors, aggravating factors, timing, and reason for visit.

In an Example 4, the method of claim 1, further comprising associating at least one sub-topic node with the at least one topic node, wherein each sub-topic node of the at least one sub-node corresponds to a sub-topic to the clinical topic.

In an Example 5, the method of Example 4, further comprising associating at least one attribute node with the at least one sub-topic node, wherein each attribute node of the at least one attribute node corresponds to a qualifying attribute for the sub-topic.

In an Example 6, the method of Example 5, wherein the knowledge graph of clinical information comprises a plurality of clinical concerns represented as modules; and wherein the method further comprises associating an attribute node of the at least one attribute node with a sub-topic node associated with another clinical concern of the plurality of clinical concerns.

In an Example 7, the method of Example 6, wherein the attribute node corresponds to at least one of the following attributes: left, right, both, and neither.

In an Example 8, the method of Example 1, wherein the association of the at least one section node with the module and the association of the at least topic node with the at least one section node is based on at least one of the following: recognized standards of care, published practice guidelines, clinical quality metrics, other sources of published clinical information, and general physician knowledge.

In an Example 9, the method of Example 8, further comprising updating the association of the at least one section node with the module and the association of the at least one topic node with the at least one section node when additional information from at least one of the following becomes available: the recognized standards of care, the published practice guidelines, the clinical quality metrics, the other sources of published clinical information, and the general physician knowledge.

In an Example 10, the method of Example 1, further comprising mapping raw data of a clinical encounter to the knowledge graph of clinical information resulting in a state of the knowledge graph pertaining to the clinical encounter.

In an Example 11, the method of Example 10, further comprising using at least one of: machine learning and natural language processing to map the raw data of the clinical encounter to the knowledge graph of the clinical information.

In an Example 12, the method of Example 10, further comprising determining whether the state of the graph resulting from the mapping of the raw data of the clinical encounter to the knowledge graph of clinical information is sufficient to calculate a clinical quality measure.

In an Example 13, the method of Example 10, further comprising determining whether the state of the graph resulting from the mapping of the raw data of the clinical encounter to the knowledge graph of clinical information is sufficient to perform population health analytics.

In an Example 14, the method of Example 10, further comprising generating electronic health record documentation based on the mapping of the knowledge graph of clinical information to the raw data of the clinical encounter.

In an Example 15, the method of Example 14, further comprising scoring the generated electronic health record documentation to determine a completeness of a patient evaluation for the clinical encounter.

In an Example 16, the method of Example 15, further comprising adapting the mapping of the knowledge graph of clinical information to the raw data of the clinical encounter to conform to an schema for the electronic health record.

In an Example 17, the method of Example 15, further comprising adapting the mapping of the knowledge graph of clinical information to the raw data of the clinical encounter to conform to interoperability standards for health information technology systems.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawings. In the figures, like reference numerals represent like elements, and the figures are to be understood as illustrative of the disclosure. The figures are not necessarily drawn to scale and are not intended to be limiting in any way.

Figure 1:
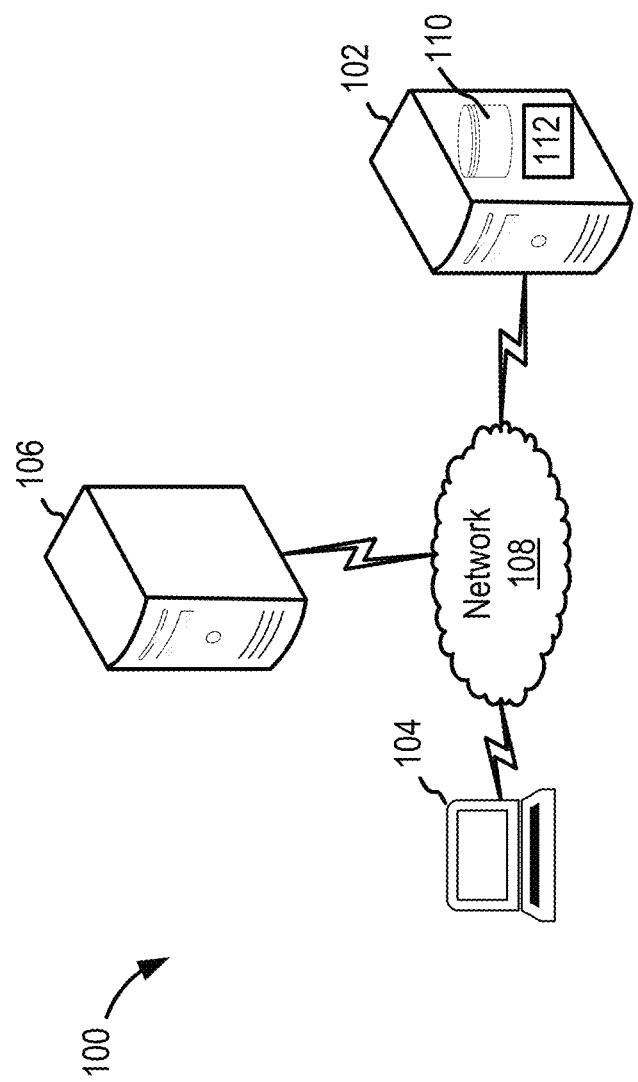
FIG. 1 is a diagram of an illustrative system configured to generate and/or apply a knowledge graph of clinical information, according to certain embodiments of the present disclosure.

While the present disclosure is amenable to various modifications and alternative forms, specific embodiments have been shown by way of example in the drawings and are described in detail below. The intention, however, is not to limit the present disclosure to the particular embodiments described. On the contrary, the present disclosure is intended to cover all modifications, equivalents, and alternatives falling within the scope of the present disclosure as defined by the appended claims.

DETAILED DESCRIPTION

In the following detailed description, reference is made to the accompanying drawings which form a part hereof, and in which is shown by way of illustration specific embodiments in which the present disclosure is practiced. These embodiments are described in sufficient detail to enable those skilled in the art to practice the present disclosure, and it is to be understood that other embodiments can be utilized and that structural changes can be made without departing from the scope of the present disclosure. Therefore, the following detailed description is not to be taken in a limiting sense, and the scope of the present disclosure is defined by the appended claims and their equivalents.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments. Furthermore, the described features, structures, or characteristics of the subject matter described herein may be combined in any suitable manner in one or more embodiments.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

As stated above, the demands for more granular, codified and/or structured data has resulted in the increase in provider data entry burden through the use of complex software and/or data entry systems, in at least some embodiments. As an example, the human hardware and/or software interface is a barrier to personalized care in many cases, and it has reduced the joy of practicing medicine and increased the frustration of providers.

According to certain embodiments, one approach to mitigating the complex data entry tasks and reducing burnout has been the use of live scribes—assistants that monitor and manage all the data entry tasks for the provider. While this approach has its benefits, it is often not automated, and this usually cannot reach highly efficient economies of scale, in certain embodiments. By fully automating the live scribe's function, one may be able to reduce provider burnout while decreasing the total cost of healthcare, given the relative efficiencies afforded to the provider when offsetting data entry tasks, according to certain embodiments.

According to certain embodiments, with the acceleration of machine learning and natural language processing, automated scribe technologies are leveraged to improve physicians' lives with an ambient solution to automate clinical documentation, significantly reducing this administrative burden which occupies nearly half their working time. According to certain embodiments of the present disclosure, a knowledge graph of clinical information is generated to facilitate automated scribe technology.

FIG. 1 is a diagram of an illustrative system 100 configured to generate and/or apply a knowledge graph of clinical information, according to certain embodiments of the present disclosure. In certain embodiments, the knowledge graph of clinical information is used by and/or incorporated into an automated scribe technology, as discussed in more detail below. This diagram is merely an example, which should not unduly limit the scope of the claims. One of ordinary skill in the art would recognize many variations, alternatives, and modifications.

According to certain embodiments, the system 100 includes a server 102 that is configured to generate a knowledge graph of clinical information. While only one server 102 is depicted, the server 102 may comprise of multiple servers.

According to certain embodiments, the server 102 stores and/or receives, from one or more user devices 104 or another server 106 via a network 108, a problem-oriented clinical knowledgebase 110. Exemplary user devices 104 include, but are not limited to, smart devices (e.g., phones, watches, speakers, etc.), computers, televisions, set-top boxes, and/or the like. The network 108 may be, or include, any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The network 108 may include a combination of multiple networks.

In certain instances, the problem-oriented clinical knowledgebase 110 is designed to serve as a source of content underlying a knowledge graph of clinical information 112, which can be used by and/or incorporated into virtual scribe technology. In some examples, this problem-oriented clinical knowledgebase 110 contains codified clinical concepts and relationships that follow clinical evidence-based best practices. For example, these codified clinical concepts and relationships are curated by clinical and informatics experts, based on published standards of care. As examples, relating concepts in this way furthers the virtual scribe technology as follows:
1. serves as a reference base of anticipated clinical concepts and their relationships to the encounter process and current topic of conversation (e.g., clinical complaint) to improve the performance of natural language understanding algorithms; and/or
2. serves as machine learning training data, to include but not limited to:
   a. feature data that consists of conversational text, which may include marked-up or tagged using natural language processing (NLP); and/or
   b. feature data that consists of the current state of an instantiated knowledge graph of clinical information, representing the sequential concepts expressed prior or just prior to current time within a given encounter or patient interview; and/or
   c. label data which consists of the specific graph nodes representative of the current input conversational text; and/or
3. establishes an initial model of clinical understanding that can be expanded upon and/or tuned via real world use and serves as a basis for continuous learning and performance tuning; according to certain embodiments, the expansion and/or tuning may be based upon but is not limited to:
   a. specific user historical use of the graph for a given problem—in this form of tuning, the user's past graph states may be used to weight the connections in the graph network (i.e., to train the machine learning (ML) model); for example, the system may be tuned to a particular user's pattern of use of the graph to help improve performance for that specific user; and/or
   b. historical use across a broader set of users to identify gaps in the graph that may serve to improve overall robustness for all users; and/or
4. provides sentence structure to aid in the generation of appropriate clinical narrative relative to the concepts expressed; and/or
5. supports the use of custom reference models that are provider-specific, including custom macros and helpers that reflect individual preferences related to intake, encounter flow and narrative output; and/or
6. enables real-time feedback as to clinical completeness and compliance with standards of care for a given complaint history or relevant plan of care.

According to certain embodiments, a technical barrier is addressed to achieving a fully automated scribe, which is, for example, called a virtual scribe, by the generation and/or application of a knowledge graph of clinical information 112, as described herein. As an example, an automated virtual scribe solution is comprised of a passive listening device that can separate speakers, identify questions and answers, and reduce a conversation to a set of related key concepts. In certain instances, these concepts, need context in terms of their relevance to the clinical concern, their relationship to the standard of care for a given problem or concern, and/or their relationship to the encounter and the resulting clinical document that is produced as a result of the clinical encounter. The knowledge graph of clinical information 112, as described herein, provides that context. In certain instances, the knowledge graph of clinical information 112 is referred to herein as the knowledge graph 112.

In certain embodiments, the knowledge graph 112 includes a set of nodes and relationships that each have specific attributes that form a clinical reference for a given clinical concern within the context of a clinical encounter. As an example, the nodes of the knowledge graph 112 are organized around a given clinical concern and/or encode the expected clinical concepts that are expressed within an encounter, their relevance, related ontology and/or codification, hierarchy, sequence and/or related expression with respect to the encounter document.

In certain embodiments, the nodes of the knowledge graph 112 are organized as modules. For example, each module is related to a given clinical concern or problem, and/or includes an array of associated keywords, diagnoses and/or affiliated specialties. As an example, the children sections (also referred to herein as section nodes, topic nodes, sub-topic nodes, attribute nodes and/or concept nodes) within a module reflect the sequential steps within an encounter and/or the sequential groups of concepts within each step that are related to the standard of care and common practice of medicine. As such, in certain examples, each clinical concept in turn is indexed to one or to many relevant clinical ontologies via its representative code or codes. In certain embodiments, the common form of expression of the clinical sections or subsections and/or concepts is also included as an attribute of each node if applicable.

In some embodiments, the resulting knowledge graph 112 creates a searchable referential map of medical knowledge and/or standards of care. For example, by structuring the information as a graph or contained within a graph database, inbound patterns of concepts generated by a natural language processing (NLP) pipeline of an automated virtual scribe system and/or generated by an engine for natural language understanding (NLU) of the automated virtual scribe system are matched to the knowledge graph 112 to yield one or more following results by the automated virtual scribe system:

1. a ranked order of modules that conform to the input pattern; and/or
2. a determination of matched concepts that link the actual input to the expected input; and/or
3. a narrative output resulting from the union of the matched concepts and steps and their associated expression attributes; and/or
4. a confirmed set of codified and structured clinical concepts and/or data determined from the conversation of the clinical concept, which can be communicated to clinical software systems in real time to trigger clinical decision support modules, and/or be stored for use later in chart communication, quality assessments and/or data analytics applications; and/or
5. a set of codified clinical data determined from clinical notes, other documents, and/or free text conversion, which can be used for knowledge extraction; and/or
6. determine and/or drive chat bot dialog questions in order to suggest and/or codify likely responses.

In certain embodiments, an automated virtual scribe system includes: (i) a passive listening device that separates speakers, identifies questions and answers, and reduces a conversation to a set of related key concepts; (ii) a database that stores a knowledge graph 112 (and/or, e.g., a knowledge graph 300 as shown in FIGS. 3-8); (iii) transforms the conversation to a set of tagged words, expressions and/or organized narrative; (iv) maps the conversation (e.g., the set of tagged words, expressions and/or organized narrative) to the knowledge graph 112 (and/or knowledge graph 300), and/or (v) the server 102 that receives the set of related key concepts, uses the stored knowledge graph 112 (and/or, e.g., a knowledge graph 300), and generates the one or more results as described above and/or generates one or more other results (e.g., the results provided in blocks 216-224).

Figure 2:
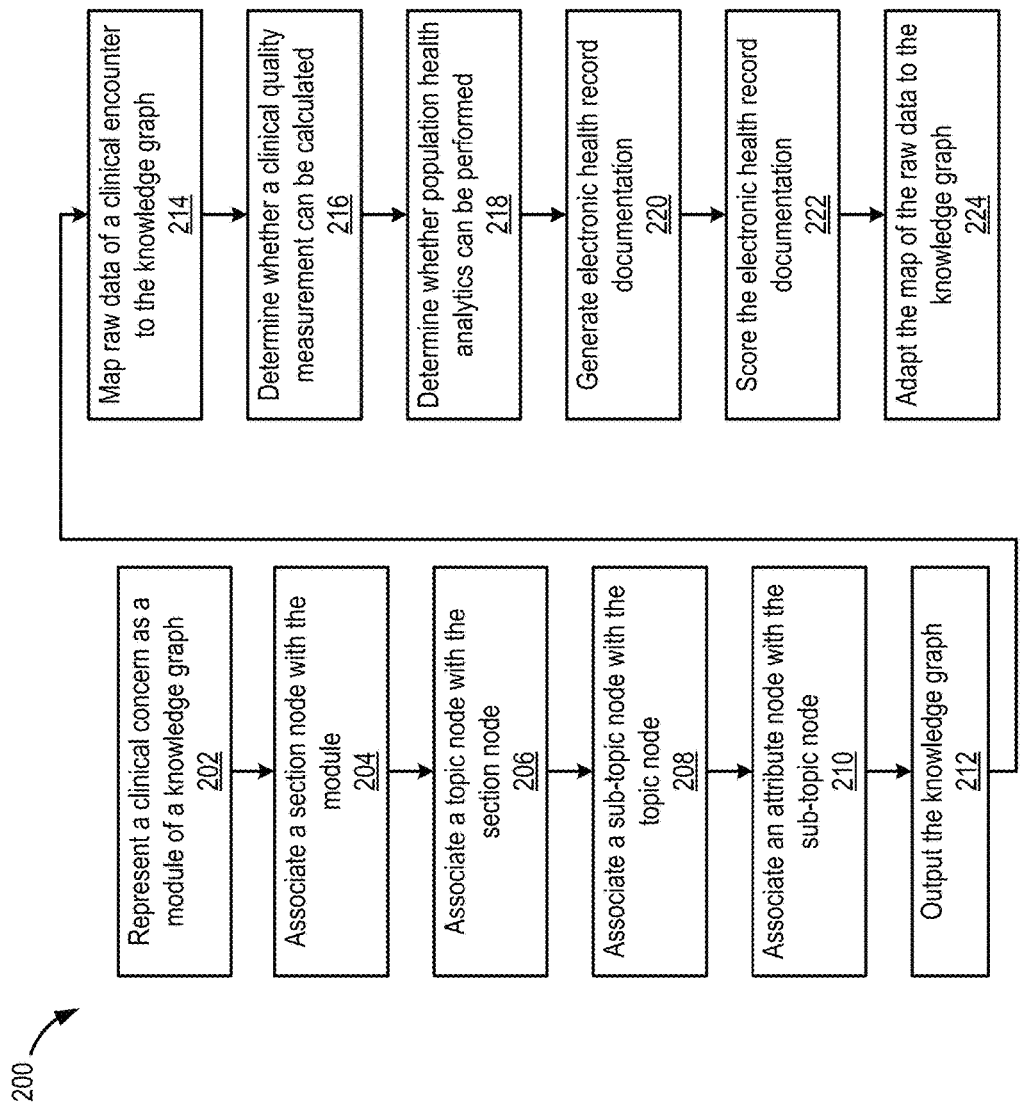
FIG. 2 is a flow diagram of an illustrative method for generating and/or applying a knowledge graph of clinical information, according to certain embodiments of the present disclosure.

FIG. 2 is a flow diagram of an illustrative method 200 for generating a knowledge graph, according to certain embodiments of the present disclosure. This diagram is merely an example, which should not unduly limit the scope of the claims. One of ordinary skill in the art would recognize many variations, alternatives, and modifications.

As illustrated, the method 200 includes representing a clinical concern as a module of the knowledge graph (block 202) and associating at least one section node with the module, wherein each section node of the at least one section node corresponds to a clinical concept relevant to the clinical concern (block 204).

In certain embodiments, the nodes of the knowledge graph (e.g., the knowledge graph 112) are organized by relationships, and a fundamental relationship that segregates the knowledge graph (e.g., the knowledge graph 112) is the clinical concern. As such, the knowledge graph (e.g., the knowledge graph 112) can be considered a problem-oriented knowledge graph with each problem consisting of a subgraph, called a module, such that each module is based upon a particular clinical problem or concern.

Figure 3:
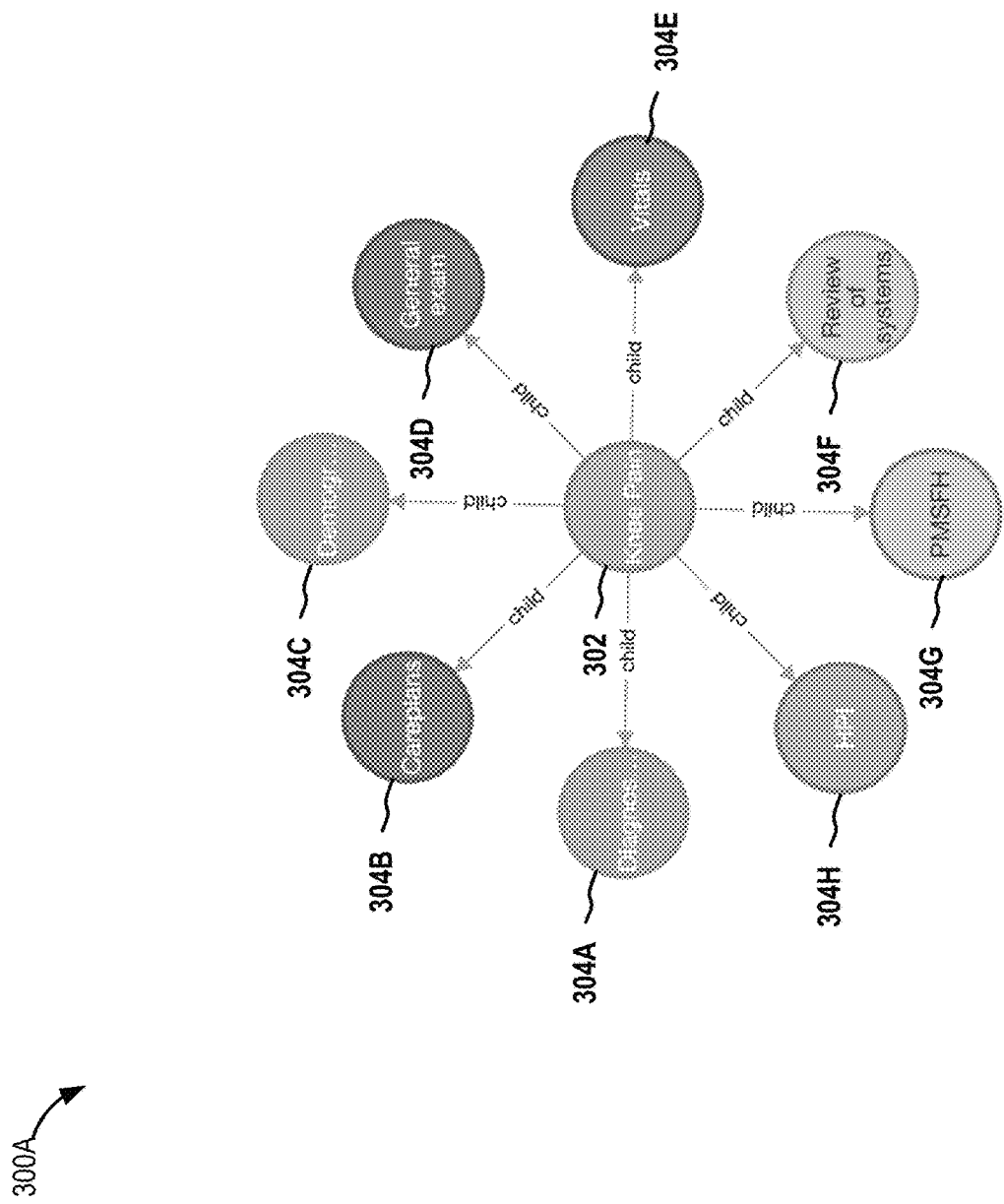
FIG. 3 illustrates a module node and section nodes of a knowledge graph of clinical information, according to certain embodiments of the present disclosure.

FIG. 3 illustrates an example of a clinical concern, e.g., knee pain, being represented as a module 302, which is the central node a knowledge graph 300A. This diagram is merely an example, which should not unduly limit the scope of the claims. One of ordinary skill in the art would recognize many variations, alternatives, and modifications.

According to certain embodiments, the portion of the knowledge graph 300A and other portions of the knowledge graph 300B-300F collectively form the knowledge graph 300 for a particular clinical concern, e.g., knee pain. And, the knowledge graphs 300 associated with each clinical concern collectively form the knowledge graph 112, in certain embodiments. Other examples of clinical concerns besides knee pain include, but are not limited to, hip pain, back pain, chest pain, skin rash, and/or fainting.

In certain embodiments, the knowledge graph 112 as a whole, and each knowledge graph 300 associated with a particularly clinical concern, are comprised of related nodes, each node representing hierarchically organized clinical concepts relevant to the clinical concern of the module 302 included in the associated knowledge graph 300. In certain embodiments, each module (e.g., module 302) and its related child nodes included in a knowledge graph for a particular clinical concern (e.g., the knowledge graph 300) is built to reflect a typical sequence and structure of a clinical encounter through additional relationships that organize relevant nodes. As such, in certain examples, each knowledge graph for a particular clinical concern (e.g., the knowledge graph 300) is generated, expanded, and/or updated using data from encounters between patients and providers.

In some examples, the knowledge graph 112 and each knowledge graph for a particular clinical concern (e.g., the knowledge graph 300) is generated, expanded, and/or updated from recognized standards of care, published practice guidelines, clinical quality metrics, other sources of published clinical information, including general physician knowledge. In certain instances, these sources change by, for example, being updated, increasing in scope, and sometimes retracted. As such, the knowledge graph 112 and each knowledge graph for a particular clinical concern (e.g., the knowledge graph 300) changes over time in response to the sources of the data changing, according to at least some embodiments.

Additionally, or alternatively, in some examples, raw data from a clinical encounter is mapped to a knowledge graph for a particular clinical concern (e.g., the knowledge graph 300) using, for example, a neural network to determine: (i) the nodes of a knowledge graph (e.g., the knowledge graph 300) pertaining to a particular clinical encounter, (ii) and/or a sequence of the nodes for a particular clinical encounter.

In the example illustrated in FIG. 3, the clinical concern and/or chief complaint represented by the module 302 is knee pain. In certain embodiments, the next set of relationships are hierarchal and are shown as section nodes 304A-304H of the encounter flow. As such, in certain embodiments, the module 302 is associated with at least one section node 304A-304H. The sections nodes 304A-304H include, for example, Diagnoses 304A, Care Plans 304B, Demographic information 304C, Examination 304D, Vitals 304E, Review of Systems (RoS) 304F, Patient History (Medical, Social, Surgical, Family, etc.) (PMSFH) 304G, and/or History of Present Illness (HPI) 304H.

In certain embodiments, the method 200 includes associating each section node 304A-304H with at least one topic node 306A-306H (block 206). Each of the at least one topic node 306A-306H is a clinical topic that relates to the encounter for a clinical concern. While clinical encounter structure and/or order may vary based on the type of encounter and/or clinical concern being addressed, in certain embodiments, there is a limited set of section nodes 304A-304H and/or topic nodes 306A-306H that can categorize the content of clinical encounters.

Figure 4:
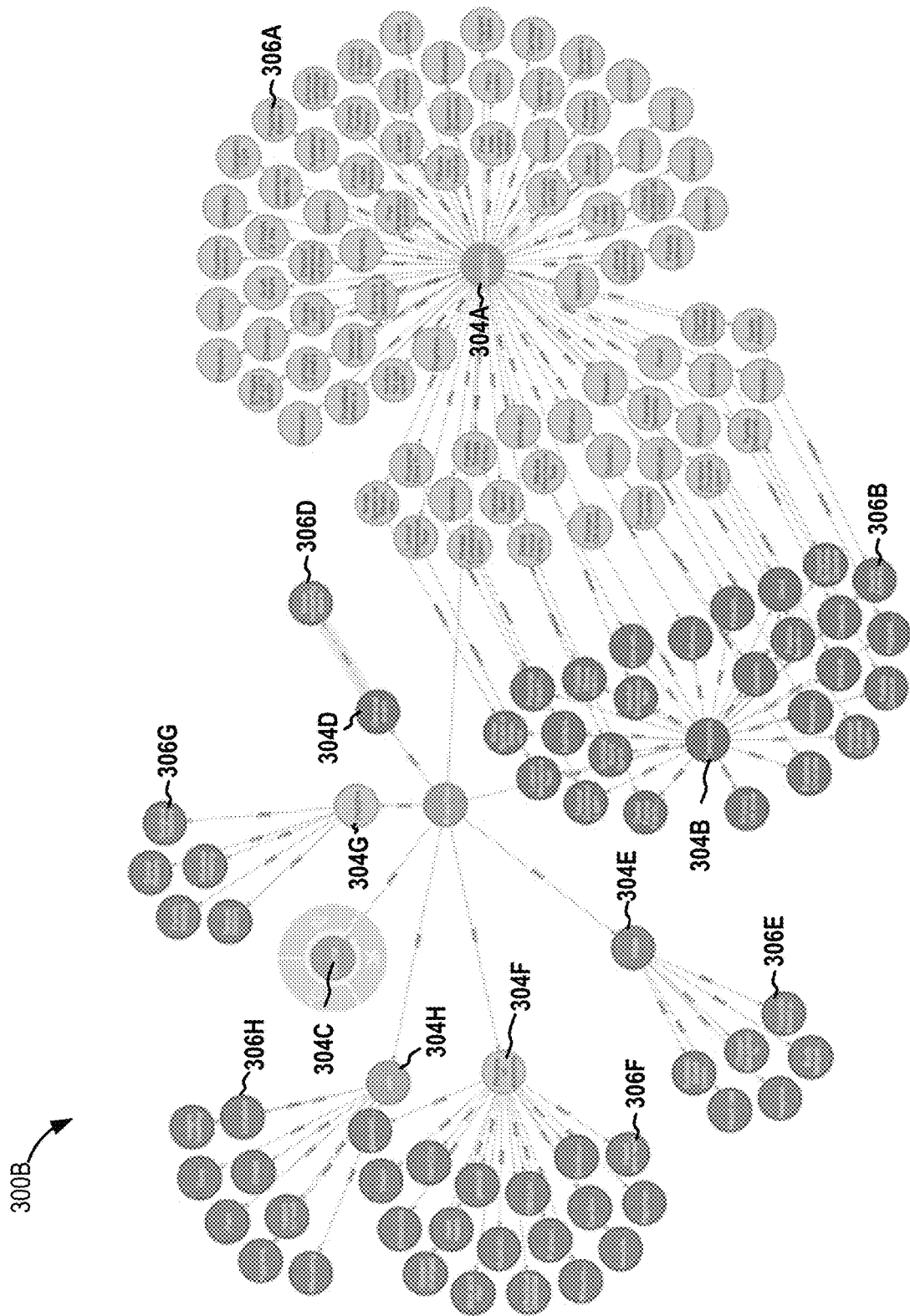
FIG. 4 illustrates topic nodes associated with section nodes of a knowledge graph of clinical information, according to certain embodiments of the present disclosure.
Figure 5:
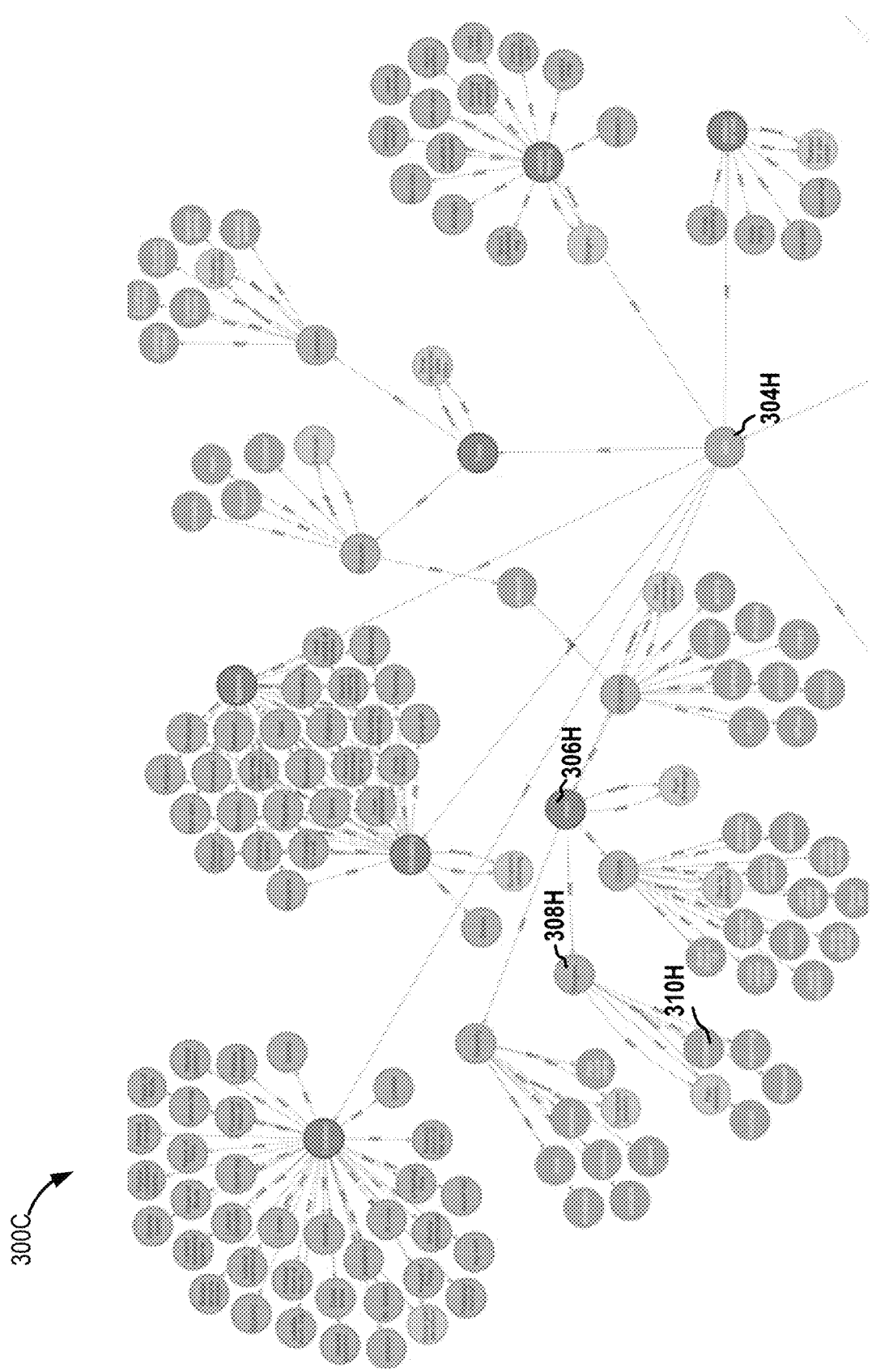
FIG. 5 illustrates a section node pertaining to History of Present Illness (HPI) and related child nodes of a knowledge graph of clinical information, according to certain embodiments of the present disclosure.
Figure 6:
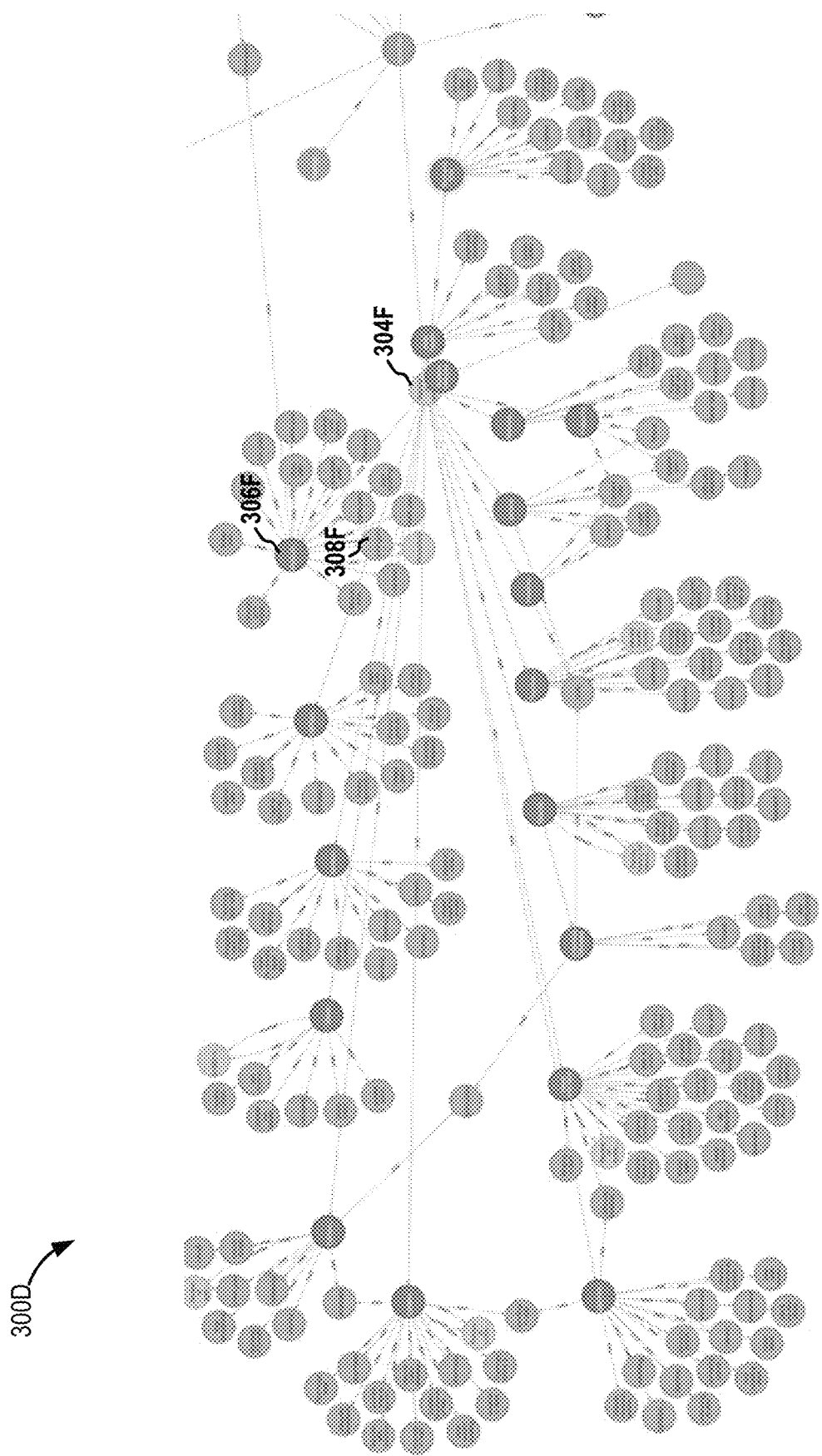
FIG. 6 illustrates a section node pertaining to Review of Systems and related child nodes of a knowledge graph of clinical information, according to certain embodiments of the present disclosure.
Figure 7:
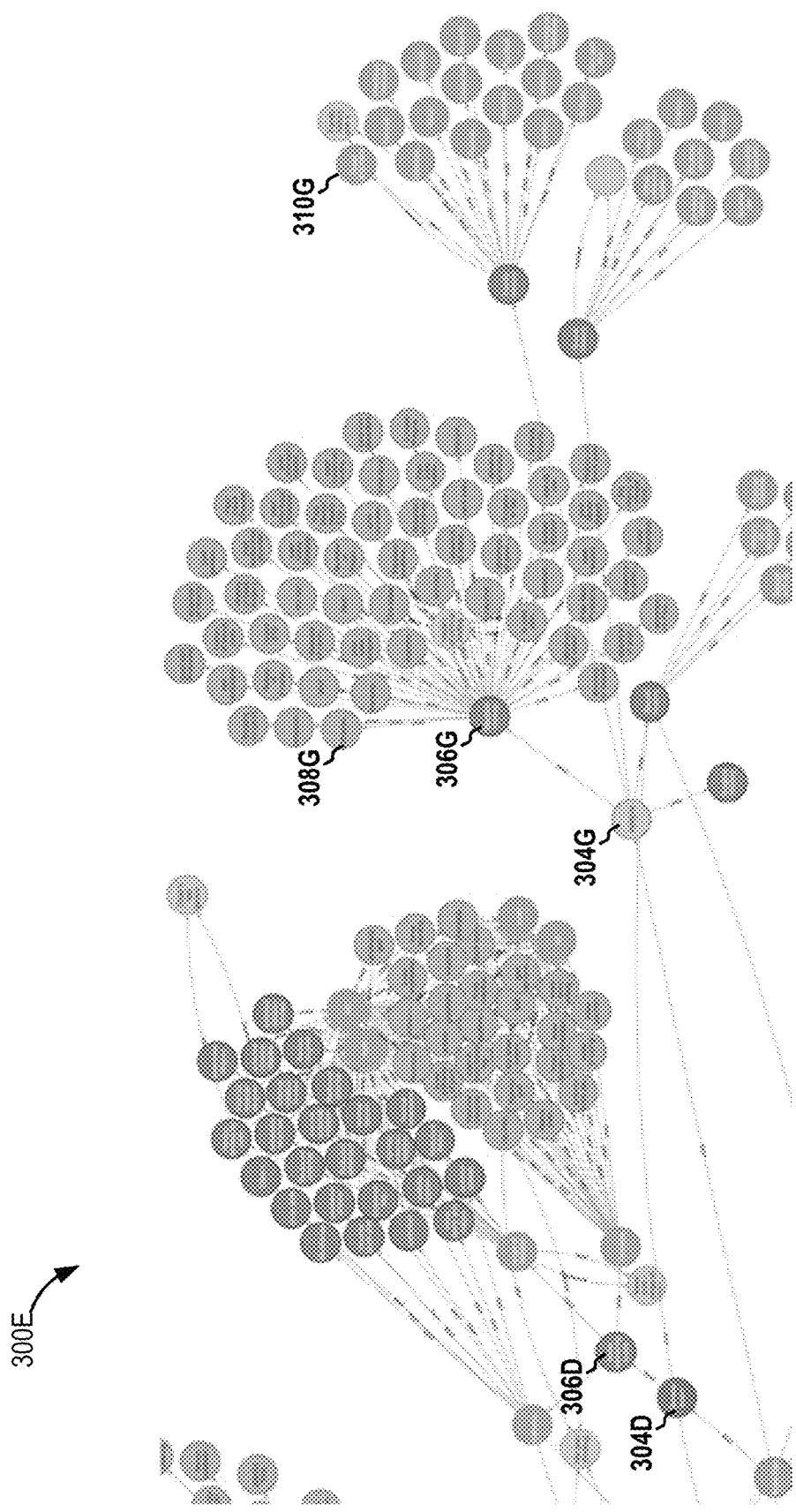
FIG. 7 illustrates section nodes pertaining to Exam and Histories and related child nodes of a knowledge graph of clinical information, according to certain embodiments of the present disclosure.
Figure 8:
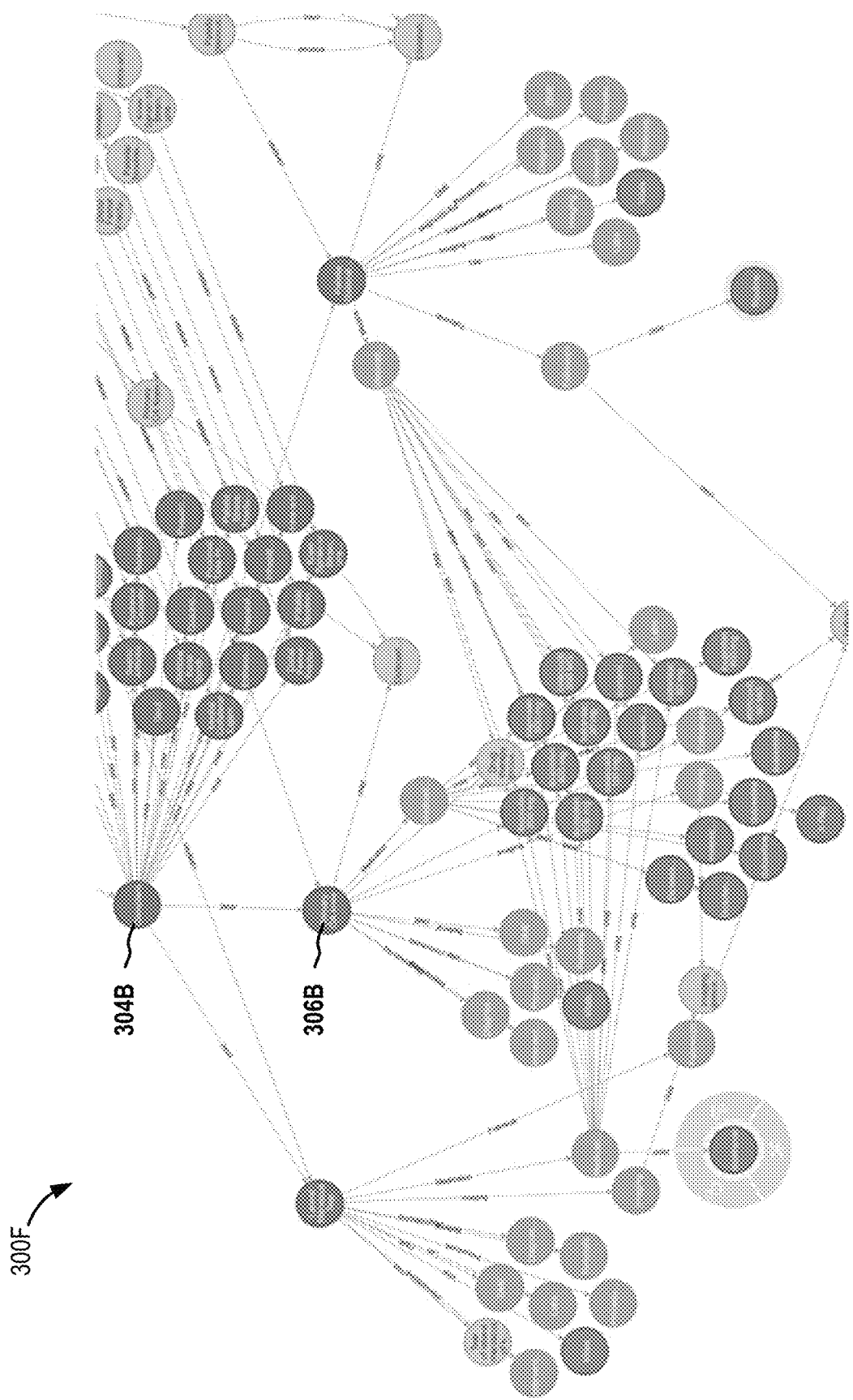
FIG. 8 illustrates a section node pertaining to Care Plans and related child nodes of a knowledge graph of clinical information, according to certain embodiments of the present disclosure.

Examples of topic nodes 306A-306H associated with each section node 304A-304H are illustrated in FIGS. 4-8. For example, FIG. 4 illustrates an example of topic nodes 306A-306H associated with section nodes 304A-304H of a knowledge graph 300; FIG. 5 illustrates an example of a section node 304H pertaining to HPI and related child nodes of a knowledge graph 300; FIG. 6 illustrates an example of a section node pertaining to RoS 304F and related child nodes of a knowledge graph; FIG. 7 illustrates examples of section nodes 304D, 304G pertaining to Exam and Histories and related child nodes of a knowledge graph; and, FIG. 8 illustrates an example of a section node 304B pertaining to Care Plans and related child nodes of a knowledge graph.

In certain examples, each section node 304A-304H and/or topic node 306A-306H has an assigned index which represents their anticipated sequence order over time. Thus, for example, the knowledge graph 300 captures many data relationships including anticipated sequence of the concepts over time for a given encounter. For example, in the HPI section node 304H, the several topic nodes 306H that are associated with the HPI section node 304H are common areas of interrogation and/or are symptoms and/or signs that relate to the HPI, such as onset, location, pain, alleviating factors, aggravating factors, timing, reason for visit, etc. As another example, the Diagnosis section node 304A, can include several topic nodes 306A that are used to represent a clinical diagnosis such as "knee sprain" or "anterior cruciate ligament injury".

According to certain embodiments, the method 200 includes associating each topic node (e.g., one or more of the topic nodes 306A-306H) with at least one sub-topic node (e.g., sub-topic node 308F, 308G and/or 308H) (block 208). Additionally, or alternatively, each sub-topic node can be directly associated with a section node (e.g., one or more of the section nodes 304A-304H) when, for example, a typical clinical encounter progresses from a section node (e.g., one or more of the section nodes 304A-304H) directly to a sub-topic node (e.g., sub-topic 308F, 308G and/or 308H).

In certain embodiments, each sub-topic node (e.g., sub-topic node 308F, 308G and/or 308H) can be a finding of a query associated with the topic node (e.g., one or more of the topic nodes 306A-306H), such as the actual onset timing, or anatomical location of the complaint. In the case of knee pain, for example, the onset can be "sudden" and the location can be "left knee". As another example, in the case of leg pain, the location can be patella, distal femur, neck of tibia, etc. In certain embodiments, this hierarchical relationship between symptom/sign and findings continues across the various nodes e.g., one or more of the nodes 302A-310H) and organizes the concepts into common collections, that are consistent with encounter flow.

According to certain embodiments, the method 200 includes associating each sub-topic node (e.g., sub-topic node 308F, 308G and/or 308H) with at least one attribute node (e.g., attribute node 310H) (block 210). Additionally, or alternatively, each attribute node (e.g., attribute node 310H) can be directly associated with a topic node (e.g., one or more of the topic nodes 306A-306H) when, for example, a typical clinical encounter progresses from a topic node (e.g., one or more of the topic nodes 306A-306H) directly to an attribute node (e.g., attribute node 310H). In certain embodiments, the at least one attribute node (e.g., attribute node 310H) is associated with multiple section nodes (e.g., multiple of the section nodes 304A-304H), topic nodes (e.g., the topic nodes 306A-306H), and/or sub-topic nodes (e.g., sub-topic node 308F, 308G and/or 308H) across the knowledge graph 300, in the event the at least one attribute node (e.g., attribute node 310H) is relevant to multiple section nodes (e.g., multiple of the section nodes 304A-304H), topic nodes (multiple of the topic nodes 306A-306H), and/or sub-topic nodes (e.g., sub-topic node 308F, 308G and/or 308H).

Examples of attributes represented by an attribute node (e.g., attribute node 310H) include, but are not limited to, left, right, neither, none, etc.

In some embodiments, one attribute of note is the textual representation for the node and its children. For example, the "onset" node mentioned above has an encoded textual attribute such as "The patient reports the <symptom> was <findings>" that is used to generate narrative in a prose that is easy to understand and is consistent with medical documentation convention.

According to certain embodiments, the method 200 includes associating one or more concept nodes with one or more of the other nodes (e.g., the nodes 302-310H) of the knowledge graph 300. In some embodiments, concept nodes represent a particular clinical concept, or other information, including, for example, specific diagnoses, procedures, medications, allergies, demographic, or clinically relevant social information. In certain embodiments, concept nodes are modified by attributed nodes, and will typically be associated with particular standard clinical code systems or ontologies. For example, wrist pain, as represented by node 308F would be an example of a granular clinical concept, that can be modified by attributes (e.g., left or right), but would not necessarily be a parent node to multiple other concepts.

In certain embodiments, one or more of the nodes (e.g., one or more of the nodes 302-310H) are associated with a codified node that corresponds to codified values of the concept in various taxonomies and/or ontologies, giving the node nodes (e.g., one or more of the nodes 302-310H) additional relationships and related concepts that are useful in finding synonyms and/or other useful properties of the codified concept.

According to some embodiments, different color nodes represent different layers (e.g., section nodes, topic, nodes, sub-topic nodes, and/or attribute nodes) of the knowledge graph 300.

According to certain embodiments, the method 200 includes outputting the knowledge graph 300 to, for example, a user device 104 (block 212).

As discussed above, in certain embodiments, the knowledge graph 112 and/or the portion of the knowledge graph 300 represents a reference set of clinically relevant concepts and relationships to a given concern. As such, according to certain embodiments, the method 200 includes mapping raw data of a clinical encounter to the knowledge graph 112 and/or 300 to semantically represent the contents of the clinical encounter (block 214). For example, for a clinical encounter, the knowledge graph 112 and/or 300 is used by an automated virtual scribe system to compare sequential output from a NLP pipeline of the automated virtual scribe system and organize these concepts in their natural relationship to the module 302 pertaining to a particular clinical concern, the section 304A-304H and/or position in the encounter flow which they are recorded for a clinical encounter, as well as their identification with respect to clinical ontologies and/or taxonomies. Stated another way, in some embodiments, a neural network is used to map the raw data from a clinical encounter to one or more of the knowledge graphs 112 and/or 300. According to certain embodiments, the neural network (e.g., a recurrent neural network (RNN)) uses sequence data from the clinical encounter in order to map the clinical encounter to the knowledge graph 300. For example, NLP software may receive and process correspondence between a provider and a patient where the patient is complaining about right knee pain. In response to the right knee pain, the provider may ask what part of the patient's right knee hurts. In one example, the patient may state the medial aspect of the patient's knee hurts. In another example, the patient may state the lateral aspect of patient's knee hurts. In practice, these different examples may result in different mappings of the clinical encounter to the knowledge graph 300. As such, in some examples, the neural network may use, as an input for one or more layers of the neural network, prior answers to inform latter connections between nodes in the neural network so that appropriate diagnosis and treatment can be rendered.

In some instances, the mapping of the raw data of a clinical encounter to the knowledge graph (e.g., knowledge graph 112 and/or 300) by, for example, a machine learning algorithm, determines the state of the knowledge graph (e.g., knowledge graph 112 and/or 300) that includes the encounter sequence context, which can be used to predict the conversational conceptual expression. For example, the state of the knowledge graph (e.g., knowledge graph 112 and/or 300) in one embodiment could be a numerical representation of a selected or mapped nodes (e.g., the nodes 302A-310H), based on encounter conversation content. This numerical representation could be expressed as a path, which is a series of numbers that represent the selected node (e.g., the nodes 302A-310H) with respect to hierarchal nodes (e.g., the nodes 302A-310H) and linking relationships. For example, an encounter that is concerned with knee pain is represented by the knowledge graph 300, such that the first few concepts expressed in conversation relates to the main symptom or complaint as knee pain, followed by pain location as right knee medial aspect, followed by associated swelling of right knee and aggravated pain on motion or weight bearing. The knowledge graph 300 state representation of this encounter may then be the paths for the nodes listed above. For example, each node path may be unique within the knowledge graph 300 and contain information that associates each selected node (e.g., the nodes 302A-310H) with the knee pain branch and related nodes (e.g., the nodes 302A-310H) that were selected in sequence. Thus, for example, the context of the chief complaint, in this case knee pain, and related children concepts are represented in sequential order as they occurred in the encounter. This context information may be used in other steps of the method 200, for example, blocks 216-224 of method 200, to gain insights into the clinical encounter that's not present in the data, as set forth below.

According to certain embodiments, once a clinical encounter and/or clinical content is mapped to the knowledge graph 112 and/or 300, the knowledge graph 112 and/or 300 state can be analyzed to yield insights regarding various healthcare functions such as, for example, whether population health analytics can be performed (block 216); and, determining population health analytics in the event healthcare analytics can be performed.

In certain instances, given the knowledge graph (e.g., knowledge graph 112 and/or 300) is embodied in the form of an object or graph database, complex pattern matching is accomplished by the automated virtual scribe system to rank the input concepts from the NLP pipeline based on the predetermined fitting clinical module or concern. For example, in the setting where multiple problems are being discussed via natural conversation, the knowledge graph (e.g., knowledge graph 112 and/or 300) is used by the automated virtual scribe system to associate the grouped concepts with the appropriate clinical concern, problem, and/or complaint. In certain embodiments, this complex pattern matching feature of the knowledge graph (e.g., knowledge graph 112 and/or 300) is leveraged by the automated virtual scribe system in several use cases, such as clinical decision support as explained below.

In certain embodiments, given the knowledge graph (e.g., knowledge graph 112 and/or 300) represents the expected standard of care for the clinical concern, it is used by the NLP pipeline of the automated virtual scribe system to act as a filter to reject noise or irrelevant input and reduce error.

According to certain embodiments, the output of the NLP pipeline (e.g., the state of the graph, including the selected and unselected nodes) serves as an input to a checklist for what is expected and can be used by the virtual scribe system to interactively guide the conversation and ensure completeness of the encounter and data capture. For example, the ability of the NLP pipeline of the automated virtual scribe system to interactively prompt the clinician and guide the conversation or confirm input matches to the clinical reference model allows for the real time verification and error correction of computed data. As such, in some embodiments, the method 200 includes determining a whether clinical quality measurement can be calculated based on the state of the graph resulting from the mapping of the raw data of the clinical encounter to the knowledge graph of clinical information (block 218). And, in embodiments where the clinical quality measurement can be calculated, the method 200 can include determining a score of the quality of the clinical encounter.

Additionally, or alternatively, the method 200 includes scoring the generated electronic health record documentation to determine a completeness of a patient evaluation for the clinical encounter (block 220).

According to certain embodiments, the method 200 includes generating electronic health record documentation based on the mapping of the raw data of the clinical encounter to the knowledge graph (block 222). For example, once the conversation is complete and the output from the NLP pipeline is mapped to the knowledge graph (e.g., the knowledge graph 112 and/or 300) by the automated virtual scribe system, the state of the mapped knowledge graph (e.g., knowledge graph 112 and/or 300) represents the current codified and structured data of the clinical encounter and is thus in a highly computable and meaningful representation. In this state, the data model of the knowledge graph (e.g., knowledge graph 112 and/or 300) is transformed to conform with the data schemas of various information systems, such as electronic medical record systems, order entry systems, clinical decision support systems, and/or quality analytics systems, in at least some embodiments. Alternatively, the knowledge graph (e.g., knowledge graph 112 and/or 300) is iterated to produce a narrative expression of the data using the textual attributes of the relevant nodes to produce an accurate clinical note or document, in at least some embodiments.

According to certain embodiments, the method 200 includes adapting the mapping of the raw data of the clinical encounter to the knowledge graph to conform to an schema for the electronic health record and/or adapting the mapping of the raw data of the clinical encounter to the knowledge graph to conform to interoperability standards for health information technology systems (block 224). For example, given the section node 304A-304H, the method 200 can include determining if the encounter conversation is conducted out of expected sequence. The knowledge graph 300 can then be used by the automated virtual scribe system to match the output from the NLP that is "out of sequence" and generate a narrative that is "in sequence".

Figure 9:
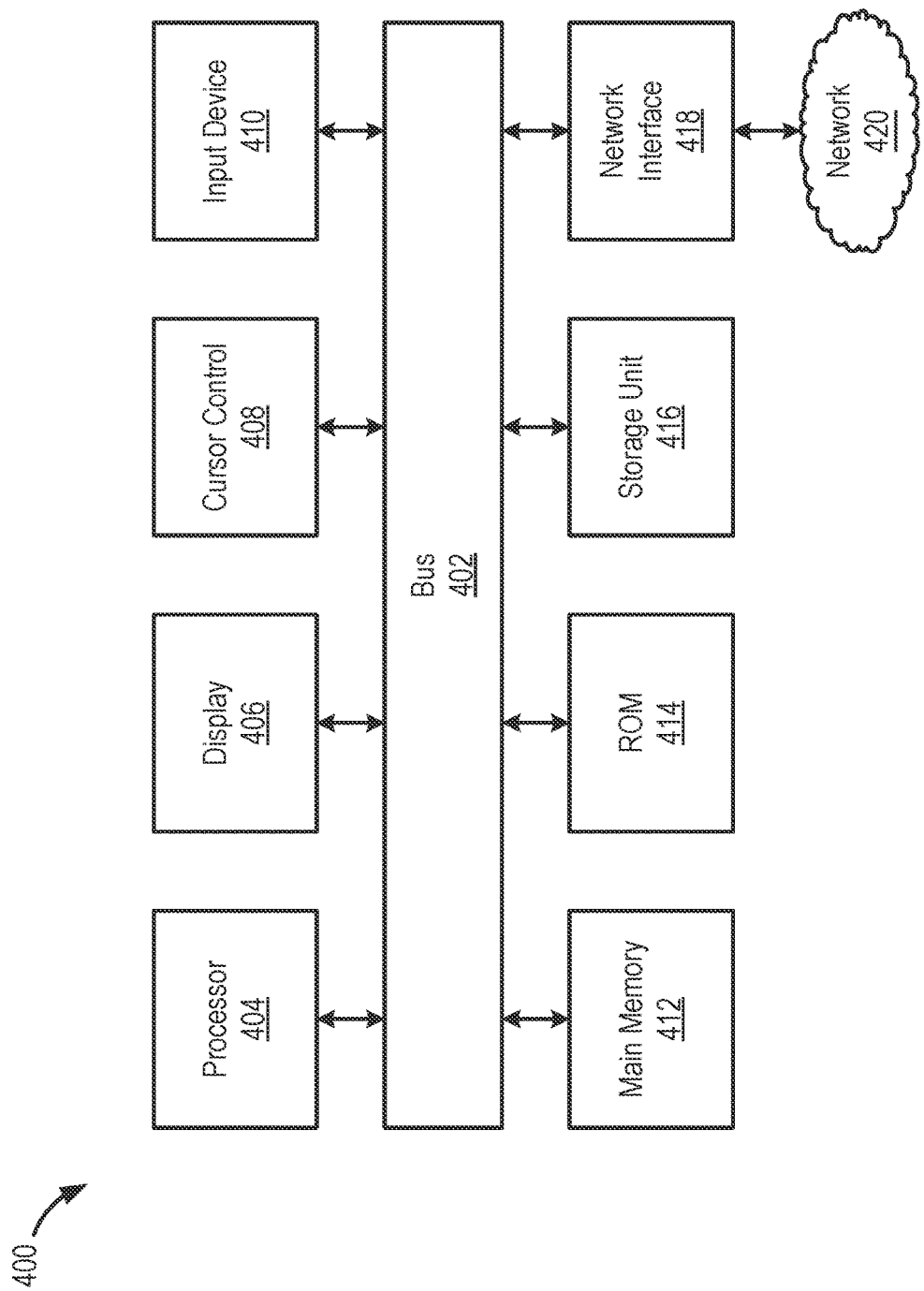
FIG. 9 is a block diagram of illustrative components of a computer system configured to generate and/or apply a knowledge graph of clinical information, according to certain embodiments of the present disclosure.

FIG. 9 is a block diagram of illustrative components of a computer system 400 for generating a knowledge graph, according to at least one embodiment of the present disclosure. For example, some or all of the processes (e.g., steps) of the method 200 are performed by the computing system 400. This diagram is merely an example, which should not unduly limit the scope of the claims. One of ordinary skill in the art would recognize many variations, alternatives, and modifications.

The computing system 400 includes a bus 402 or other communication mechanism for communicating information between, a processor 404, a display 406, a cursor control component 408, an input device 410, a main memory 412, a read only memory (ROM) 414, a storage unit 416, and/or a network interface 418. In some examples, the bus 402 is coupled to the processor 404, the display 406, the cursor control component 408, the input device 410, the main memory 412, the read only memory (ROM) 414, the storage unit 416, and/or the network interface 418. And, in certain examples, the network interface 418 is coupled to a network 420 (e.g., the network 108).

In some examples, the processor 404 includes one or more general purpose microprocessors. In some examples, the main memory 412 (e.g., random access memory (RAM), cache and/or other dynamic storage devices) is configured to store information and instructions to be executed by the processor 404. In certain examples, the main memory 412 is configured to store temporary variables or other intermediate information during execution of instructions to be executed by processor 404. For example, the instructions, when stored in the storage unit 416 accessible to processor 404, render the computing system 400 into a special-purpose machine that is customized to perform the operations specified in the instructions (e.g., the method 200). In some examples, the ROM 414 is configured to store static information and instructions for the processor 404. In certain examples, the storage unit 416 (e.g., a magnetic disk, optical disk, or flash drive) is configured to store information and instructions.

In some embodiments, the display 406 (e.g., a cathode ray tube (CRT), an LCD display, or a touch screen) is configured to display information to a user of the computing system 400. In some examples, the input device 410 (e.g., alphanumeric and other keys) is configured to communicate information and commands to the processor 404. For example, the cursor control 408 (e.g., a mouse, a trackball, or cursor direction keys) is configured to communicate additional information and commands (e.g., to control cursor movements on the display 406) to the processor 404.

Additionally, or alternatively, the methods and systems described herein may be implemented on many different types of processing devices by program code comprising program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation, and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations, one or more features from a combination can in some cases be removed from the combination, and a combination may, for example, be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for generating a knowledge graph of clinical information for use as a reference model to semantically represent relevant information from clinical encounters, the method comprising:
   representing a clinical concern as a module of the knowledge graph of clinical information;
   associating at least one section node with the module, wherein each section node of the at least one section node corresponds to a clinical concept relevant to the clinical concern;
   associating at least one topic node with the at least one section node, wherein each topic node of the at least one topic node corresponds to a clinical topic relevant to the clinical concept;
   mapping raw data of a clinical encounter to the knowledge graph of clinical information resulting in a state of the knowledge graph pertaining to the clinical encounter;
   outputting the knowledge graph of clinical information to semantically represent the relevant information from the clinical encounter associated with the clinical concern;
   generating electronic health record documentation based on the mapping of the knowledge graph of clinical information to the raw data of the clinical encounter; and
   scoring the generated electronic health record documentation to determine a completeness of a patient evaluation for the clinical encounter.

2. The method of claim 1, wherein the at least one section node corresponds to at least one of the following clinical concepts: history of present illness, review of systems, examination, history, diagnosis, and care plan.

3. The method of claim 1, wherein the at least one topic node corresponds to at least one of the following clinical topics: onset, location, pain, alleviating factors, aggravating factors, timing, and reason for visit.

4. The method of claim 1, further comprising associating at least one sub-topic node with the at least one topic node, wherein each sub-topic node of the at least one sub-node corresponds to a sub-topic to the clinical topic.

5. The method of claim 4, further comprising associating at least one attribute node with the at least one sub-topic node, wherein each attribute node of the at least one attribute node corresponds to a qualifying attribute for the sub-topic.

6. The method of claim 5, wherein the knowledge graph of clinical information comprises a plurality of clinical concerns represented as modules; and wherein the method further comprises associating an attribute node of the at least one attribute node with a sub-topic node associated with another clinical concern of the plurality of clinical concerns.

7. The method of claim 6, wherein the attribute node corresponds to at least one of the following attributes: left, right, both, and neither.

8. The method of claim 1, wherein the association of the at least one section node with the module and the association of the at least topic node with the at least one section node is based on at least one of the following: recognized standards of care, published practice guidelines, clinical quality metrics, other sources of published clinical information, and general physician knowledge.

9. The method of claim 8, further comprising updating the association of the at least one section node with the module and the association of the at least one topic node with the at least one section node when additional information from at least one of the following becomes available: the recognized standards of care, the published practice guidelines, the clinical quality metrics, the other sources of published clinical information, and the general physician knowledge.

10. The method of claim 1, further comprising using at least one of: machine learning and natural language processing to map the raw data of the clinical encounter to the knowledge graph of the clinical information.

11. The method of claim 1, further comprising determining whether the state of the graph resulting from the mapping of the raw data of the clinical encounter to the knowledge graph of clinical information is sufficient to calculate a clinical quality measure.

12. The method of claim 1, further comprising determining whether the state of the graph resulting from the mapping of the raw data of the clinical encounter to the knowledge graph of clinical information is sufficient to perform population health analytics.

13. The method of claim 1, further comprising adapting the mapping of the knowledge graph of clinical information to the raw data of the clinical encounter to conform to an schema for the electronic health record.

14. The method of claim 1, further comprising adapting the mapping of the knowledge graph of clinical information to the raw data of the clinical encounter to conform to interoperability standards for health information technology systems.

* * * * *